United States Patent
Fraser et al.

(10) Patent No.: US 7,585,624 B2
(45) Date of Patent: Sep. 8, 2009

(54) DETECTION OF THE ENERGY OF PHOTONS FROM BIOLOGICAL ASSAYS

(75) Inventors: George William Fraser, Leicester (GB); Andrew David Holland, Northampton (GB); Gertrude Maria Schwarzacher, Leicester (GB); John Seymour Heslop-Harrison, Leicester (GB)

(73) Assignee: University of Leicester (GB)

( * ) Notice: Subject to any disclaimer, the term of this patent is extended or adjusted under 35 U.S.C. 154(b) by 494 days.

(21) Appl. No.: 10/794,397

(22) Filed: Mar. 5, 2004

(65) Prior Publication Data

US 2005/0014171 A1 Jan. 20, 2005

Related U.S. Application Data

(63) Continuation of application No. PCT/GB02/04019, filed on Sep. 5, 2002.

(30) Foreign Application Priority Data

Sep. 7, 2001 (GB) ................. 0121700.9

(51) Int. Cl.
C12Q 1/68 (2006.01)
G01N 33/53 (2006.01)
C07H 21/04 (2006.01)
C07H 21/00 (2006.01)
C07H 19/04 (2006.01)

(52) U.S. Cl. .................. 435/6; 435/7.1; 536/24.3; 536/25.32; 536/26.6

(58) Field of Classification Search .................. 435/6, 435/7.1, 91.1, 183, 283.1, 287.1, 287.2, 968; 536/23.1, 24.3, 24.33, 25.3, 25.32, 26.6; 530/300, 350; 8/648; 156/67; 436/546
See application file for complete search history.

(56) References Cited

U.S. PATENT DOCUMENTS

| 4,791,585 | A | 12/1988 | Maki et al. |
| 4,922,092 | A | 5/1990 | Rushbrooke et al. |
| 5,061,076 | A | 10/1991 | Hurley ................. 356/417 |
| 5,389,792 | A * | 2/1995 | DiMarzio et al. ...... 250/370.06 |
| 5,776,674 | A * | 7/1998 | Ulmer ................. 435/6 |
| 5,784,162 | A | 7/1998 | Cabib et al. ............. 356/346 |
| 5,994,694 | A | 11/1999 | Frank et al. ............. 250/281 |
| 6,211,519 | B1 | 4/2001 | Nam et al. ............. 250/336.2 |

(Continued)

FOREIGN PATENT DOCUMENTS

EP 851228 A1 7/1998

(Continued)

OTHER PUBLICATIONS

Rando, N , et al., "Detection of Optical Photons with Superconducting Tunnel Junction Detectors", *Nuclear Instruments and Methods in Physics Research*, vol. A370, (1996), pp. 85-87.

(Continued)

*Primary Examiner*—Frank W Lu
(74) *Attorney, Agent, or Firm*—Schwegman, Lundberg & Woessner, P.A.

(57) ABSTRACT

A cryogenic detector is used for detection in a biological assay.

16 Claims, 9 Drawing Sheets

U.S. PATENT DOCUMENTS

| | | | |
|---|---|---|---|
| 6,263,095 B1 | 7/2001 | Rushbrooke et al. | 382/128 |
| 6,355,420 B1 * | 3/2002 | Chan | 435/6 |

FOREIGN PATENT DOCUMENTS

| | | |
|---|---|---|
| EP | 1026260 A1 | 8/2000 |
| GB | 2315131 | 1/1998 |
| JP | 7239291 | 9/1995 |
| JP | 63090765 | 4/1998 |

OTHER PUBLICATIONS

"Spin-Off Successes—Preparing for the Future", Copyright © 1999, European Space Agency,(Jun. 1999), 36 pgs.

Irwin, K. D., "Seeing With Superconductors", *Scientific American*, (2006), 62-69.

Labov, S. E., et al., "Cryogenic Detector Development at LLNL: Ultraviolet, X-ray and Biomolecule Spectroscopy", *Seventh International Workshop on Low Temperature Detectors* (Jul. 27-Aug. 2, 1997), [online]. [archived Sep. 10, 2003]. Retrieved from the Internet: <URL: http://web.archive.org/web/20030910231939/http://www.llnl.gov/tid/lof/documents/pdf/231603.pdf>, 16 pgs.

Malbet, F., et al., "Integrated Optics for Astronomical Interferometry—I. Concept and Astronomical Applications", *Astronomy & Astrophysics, Supplement Series*, 138, (1998), 135-145.

Peacock, T., et al., "Recent Developments in Superconducting Tunnel Junctions for Ultraviolet, Optical & Near Infrared Astronomy", *Astronomy & Astrophysics Supplement Series*, 127, (1998), 497-504.

Prober, D. E., "To Catch a Photon", *Nature*, vol. 425, (2003),777-778.

Schena, M., et al., In: *DNA Microarrays—A Practical Approach*, Oxford University Press, New York, NY (1999), 10-42.

\* cited by examiner

DETECTION OF THE ENERGY OF PHOTONS FROM BIOLOGICAL ASSAYS

RELATED APPLICATIONS

This application is a Continuation Under 35 U.S.C. 111(a) of PCT/GB02/04019, filed on Sep. 5, 2002, and published in English on Mar. 20, 2003 as WO 03/023376 A1, which claimed priority under 35 U.S.C. 119 of United Kingdom Application No. 0121700.9, filed Sep. 7, 2001, which applications and publication are incorporated herein by reference.

The present invention relates to the detection of the energy of photons from biological assays, including those giving rise to characteristic transmission, reflectance and absorbance spectra. More particularly but not exclusively, the present invention relates to the detection of fluorescence, and especially the detection of fluorescence-labelled biological samples. In an important aspect, the present invention relates to detection of fluorescence in nucleic acid hybridisation arrays.

BACKGROUND OF THE INVENTION

Imaging of the hybridisation of nucleic acid probes including probes to nucleic acid targets including DNA targets is a key technology of modern biology, underpinning molecular, genomic and nucleic acid/DNA diagnostic methods.

Radiolabelling is one option, such as for membrane hybridisation, but it is difficult to extract quantitative results and to differentiate multiple labels. Fluorochrome methods offer advantages, especially with systems using optical lenses including microarrays, microscopes and flow cytometers. Various technologies have been used in biology for fluorescence wavelength detection, including dichoroic bandpass emission filters, emission-prism systems, grating methods and Raman spectroscopy. At least the first three have been applied to microarray readout systems.

Illustratively, reference is made to U.S. Pat. No. 5,784,162 which describes spectral bioimaging methods for biological research, medical diagnostics and therapy. The system consists of an exciting light source; a biological target (which might be a microarray) labelled with two or more fluorochromes; collecting optics; an interferometer; exit optics; and a two-dimensional array of detector systems. For a microarray experiment with two fluorochromes, with peak emissions at wavelengths $L_1$ and $L_2$ and characteristic excitation and emission spectra, the result of the experiment may be, for example, the difference in intensities;

$$D=I(L_1)-I(L_2)$$

The spectrometer elements can be arranged so that the signal arriving at each pixel of the output detector is proportional to the density difference D emitted from a given point in the sample. The D intensity scale is then mapped onto a false colour scale for display, so that for example a point for which $I(L_1)\gg I(L_2)$ will appear red and so on. The system relies on using the interferometer to construct linear combinations of intensities emitted at specific wavelengths.

The present invention offers a new development in detection systems for biological assays.

SUMMARY OF THE INVENTION

According to the present invention, we employ a cryogenic detector in a biological assay. A cryogenic detector operates at a temperature where the photon capture element is operating close to or below that temperature at which it exhibits superconductimg properties. Such a detector can detect the energy of photons from biological assays, notably those giving rise to changes in fluorescence. The invention is not restricted to fluorescence, and cryogenic detectors can be used more generally in biological assays giving rise to characteristic transmission, reflectance and adsorbance spectra.

A cryogenic detector typically operates at a temperature below 1 K and can count optical photons and resolve their energy. Cryogenic detectors are known for use in astronomy. Reference is made, for example, to N. Rando et al., Experimental Astronomy 10 (4) (2000) 499-517. We now use such a cryogenic detector to tag each photon from a fluorochrome or other source, typically by logging time of arrival, energy, as well as x and y co-ordinates.

The invention offers high sensitivity and accurate quantification for bioimaging, particularly for the parallel registration of fluorescence from several different probes in hybridisation assays such as occurs with gene chips or arrays, as well as for membrane hybridisation, tissues and cells.

A biological assay of this invention typically involves specific binding of an analyte to a binding partner, and detection of photons indicative of the binding event. One of the binding partners can be immobilised by binding to a support. One of the binding partners can be labelled with a fluorochrome or other photon emitter.

DETAILS OF THE INVENTION

Optical photon-counting with superconducting tunnel junctions (STJs) was first described by A. Peacock et al., Nature 381 (1996) 135. The present state of the art (6×6 array of tantalum devices) is given in the Rando et al. paper, Experimental Astronomy 10 (4) (2000) 499-517. The final figure of this paper illustrates the potential improvement in performance in going to hafnium or molybdenum-based systems.

Superconducting tunnel junctions are not the only kind of cryogenic detectors which we can employ to give wavelength resolution in the optical. Another candidate is the Transition Edge Sensor (TES), whose application in the optical is described by B. Cabrera et al., Applied Physics Letters 73 (6) (1998) 735.

In accordance with the present invention, a cryogenic detector based on conventional metal superconductors suitably operates at a temperature typically below 1 K, usually below 500 mK, and possibly below 300 mK or 100 mK or even 10 mK.

Usually fluorescent light is transmitted to the cryogenic detector using an optical fibre. The optical fibre is warmer than the cryostat, with an effective temperature at the warm end of around say 293 K. The optical fibre is thereby a black body emitter of radiation with a precise spectral form that provides a calibration signal. The system is thus self-calibrating.

Rough calculations suggest that a cryogenic STJ detector is in the region of 150 to 200 times more sensitive than an existing optical photon counting (but not energy resolving) detector using a transmission photocathode such as the multialkali antimonide S20.

Current tantalum-based STJs offer resolving powers in the optical $\lambda/\delta\lambda$ of about 10. This would allow say 3 or 4 fluorochromes to be imaged at one time, provided that they were carefully chosen to have maximum spectral separation. Improved data analysis, event discrimination and particularly next generation devices based on (for example) the superconductor hafnium might yield resolving powers $\lambda/\delta\lambda$ of the order of 50 and a consequent increase in fluorochromes from 3 or 4 to say 10 to 15 or more.

Thus, cryogenic detectors allow multiple different fluorochromes or other fluorescent sources to be resolved at the same time, so that more information can be obtained in a shorter time. The different fluorochromes can be distinguished from each other by one or more of (a) excitation spectrum, (b) emission spectrum, (c) the time between excitation and emission. The use of time resolution (the time gap between excitation and emission) as a way of distinguishing fluorochromes and as a way of distinguishing sample fluorescence from substrate or endogenous (colloquially termed "background") fluorescence/luminescence is especially appropriate for resolving multiple fluorochromes.

There are many known fluorochromes which are not routinely used at present, because of too small a gap between excitation wavelength and emission wavelength (Stokes Shift) or because of low efficiency of fluorescence (i.e. low level of brightness), or the narrow band nature of fluorochromes, but these will not be problems for the new detector capabilities. Thus, in one aspect, this invention employs multiple fluorochromes unsuited for conventional detection systems using for example photomultiplier tubes (PMTs) and image intensifiers but which are suited for cryogenic detection.

Time resolution (time gated detection) of the fluorescence is a very important feature to minimize background and allow choice in substrates, preparation and hybridisation methods. As well as excitation and emission wavelengths, each fluorescent molecule has a characteristic time between excitation and emission and this could be exploited to resolve further fluorochromes. Most (auto)fluorescence from substrates and samples will have a different time delay from the probe fluorochromes and this can be gated out. Time resolution also simplifies filters in the light path, since there is no reflected light signal from the specimen going into the detector path. The times vary in the order of ps (picoseconds) to hundreds of ns, typically 10 to 100 nsec. Relatively large bandwidths of signals might be coped with: current cameras are 12 bit, although within this it is rarely necessary to use more than 8 bits. However, different fluorochromes on one slide may vary in brightness over a 14 bit range, and a suitable detector is then needed.

Fluorochromes are currently designed to have high brightness (efficiency of fluorescence), large Stokes-shift (wavelength gap between excitation and emission), excitation at major mercury bulb or laser wavelengths, and high stability under illumination. In our technology, these considerations may change. With photon counting, brightness may not matter, time resolution may mean small shifts can be used, and it may be helpful to design a full family of fluorochromes with a single excitation source, whether laser, or bulb, incorporating filters or not.

Cryogenic detectors allow high-sensitivity, quantifiable analysis of information from gene arrays or other hybridisation systems, in a way that analyses a great deal more information than is currently possible at any given time. We envisage the use of more than one fluorochrome, with perhaps at least 3, 4 or 5, preferably at least 10, and more preferably at least 15 different fluorochromes.

Examples of particular fluorochromes that might be employed include the cyanine dyes (for example Cy3, Cy3.5, Cy5, from Amersham Company, although cyanine is a generic group of fluorophores from around the 1950s), the Alexa series of dyes from Molecular Probes company, or the Spectrum dyes from Vysis company. Other, older fluorochromes include Texas Red and fluorescein.

The fluorochrome molecules are typically commercially available in a form conjugated to a nucleotide (DNA component) and incorporated into the probe DNA using enzymes. Some non-enzymatic methods are also available for incorporation, and, particularly for diagnostic applications, the labelled probe may be employed.

Apart from parallel registration of fluorescence from several probes in hybridisation assays (gene chips or arrays), the present invention is suited for imaging of developed versions of membrane (Southern) hybridisations and other hybridisation procedures. Moreover, the cryogenic detectors can be used to quantify fluorescent markers other than those for hybridization of DNA probes. Other examples include:

1) molecules which change their conformation and hence fluorescence when they associate with the target (e.g. DNA, proteins, cellulose). In the DNA array situation, the amount of DNA on each spot can be quantified using fluorochromes such as DAPI, Hoechst 33258, pararosaniline, chromomycinA$_3$ or the PoPo, BoBo, ToTo series from Molecular Probes;

2) fluorescent indicators (change fluorescence in the presence of ions, e.g. hydrogen ions to measure pH, or calcium);

3) biological molecules or structures which themselves fluoresce—red blood cells and chloroplasts are examples, the fluorescence of both of which is affected by disease;

4) parallel technologies to the DNA arrays using protein arrays and fluorescently labelled antibodies.

5) characterising fluorescence emission spectra from labels and biological molecules.

6) measuring the absorbance of light by biological molecules and structures (e.g. of DNA and RNA).

For membrane-based (Southern and allied) hybridisation, a micro-technology might be developed to work on the area of a few square centimeters. With robotic loading systems becoming widely available, loading tracks on a small area gel is little problem, and thin substrates and short runs are very advantageous. With the possibility of multiple fluorescent probes, stripping of radioactive probes becomes unnecessary, and even hybridisation to DNA immobilized in dried-gels is usable, or indeed real-time imaging as fluorescent bands pass the detector as in ABI DNA sequencing machines.

At its most basic, in one aspect, the present invention involves providing a nucleic acid binding partner on a matrix, hybridising it with a fluorochrome-labelled probe, then illuminating with an excitation light (matched to the fluorochrome, which can be chosen to be excited between typically UV and yellow as required), and measuring the emission spectrum. In essence this would use the system as a spectrophotometer. In another mode, a very small number of photons may be analysed, not enough to provide a spectrum, but their characteristics provided from the cryogenic detector will allow the molecular source of the photons to be determined.

For high throughput, it is currently preferred to have a continuous system rather than a batch-oriented system. For this aspect of the invention, the substrate with immobilised DNA might be a strip of flexible/rollable substrate (such as nylon membrane) many meters long with targets placed on it one or a few wide (and for example with a bar code along the side to identify each sample). Such an approach would vastly simplify the robotics to place the samples and move the surface past the detector. Care is needed to give compatibility with the procedures making synthetic probes on the substrate surface (typically photosensitive/photolithography methods). It would be even better to do everything in fluids, because precipitation and drying of DNA onto substrates is an awkward process, with losses of target, and running solutions over the immobilised target (e.g. DNA) is hard to control automatically. Systems of valves and pumps would be easiest to make: perhaps large molecules could be held in a gel while small molecules (probes) can be diffused in and washed out, leaving those forming hybrids behind in a format that can be pumped around and through detectors.

As one illustration of a possible use of the present invention, arrays in the form of chips can identify cancer-related genes in a group of patients. A large selection of cancer-related genes are secured to the chip, and DNA samples from say 20 patients at once can all be put on one chip for analysis, with each DNA sample having its own fluorochrome distinguishable from all the others. All patients can therefore be analysed at the same time using the same chip. This ability for multiple probe-targets using multiple fluorochromes is a significant advance over anything already being done.

Furthermore, one of the key needs for more colours is to include controls, that is samples where the result is known. For example, rather than screening 20 patients, one might include several (4 to 6) samples from the candidate tumour of one patient, some non-tumour DNA from the same patient, and then different types/stages of tumour DNA from diagnosed cases. With more colours, then extra real samples can be added, making more efficient use of the controls.

In one embodiment, the present invention involves a system to image fluorescence from hybridisation of multiple probes to DNA on a microscope slide, in typically 10 nm wide channels across the visible, near-IR and near-UV wavelengths, in a pixel-based system with high speed, time-resolution, and pixel sizes down to say 10 µm (microns) square or less. The size required for scanning might be an area of 22 mm×44 mm on a 1"×3" standard microscope slide format. Different strategies for excitation are possible. Multiple photon excitation such two-photon excitation of fluorochromes, as in confocal microscopes, will allow laser diodes. In a typical arrangement, the detector can be static and with the light from sample cells rastered a row at a time onto a linear array of superconducting tunnel junctions. In a typical arrangement, each element of the array essentially has its own fibre optic filament going to it, and the array can be one (linear) or two (planar) dimensional. Fibres from defective array elements ('pixels') can be omitted. Alternatively, it may be possible to focus the whole image onto an array (as in a conventional camera). The fibre optic cables can be sited long distances from the reading instrument and are not limited to arising from a single instrument, and might be linked to different types of instrument simultaneously, even located in different laboratories or buildings Resolution is preferably at least 5 µm (i.e. 200×200 per mm$^2$), with increase to perhaps 0.2 µm being ideal (i.e. the theoretical limit of light microscopy). For finding the specimen on the slide, scanning with 100 µm resolution is required, and then with 30-40 µm for preliminary analysis. One design possibility with a linear or area array sensor is to start with a 256-element array, and then consider an increase by 8 or 16 fold.

In other embodiments of the invention, the cryogenic detector is applied to fluorescence or confocal microscopes, or as the detector of fluorescence, backscatter, sidescatter and absorbance on a flow cytometer analysing properties of cells or cellular components in suspension.

The output from the imaging device will be essentially a spectrum, wavelength, or photon energy histogram for each pixel at each excitation wavelength (so at least five dimensions: X and Y of the pixel, excitation wavelength, emission wavelength and time between excitation and emission). Software can then calculate the contribution of each fluorochrome.

More generally, the present invention provides a system for performing biological assays which includes data capture equipment and data processing software. The system may further include means for generating a display or print indicative of the results of the assay.

With the present invention, a cryogenic detector is typically used to detect fluorescence such as may occur with probe hybridisation using fluorochrome labels, though the invention is not tied to fluorescence arising from labels, since we also envisage detection of transmission/reflectance/autofluorescence/absorbance spectrum ('colour'). The invention also extends to stimulated emission spectra other than fluorescence, and includes photon emission from electronic chromaphores, such as those based on polymers or dendrimers. These electronic chromaphores emit visible photons in response to electrical energy input, currently the basis of new flat screen display technology. Fabrication techniques developed for these products married to conventional gene chips can provide devices where the light emitted varies with applied voltage, thus providing a measure of the biological targets with which the chromaphore is associated.

DRAWINGS OF THE INVENTION

Figure 5:
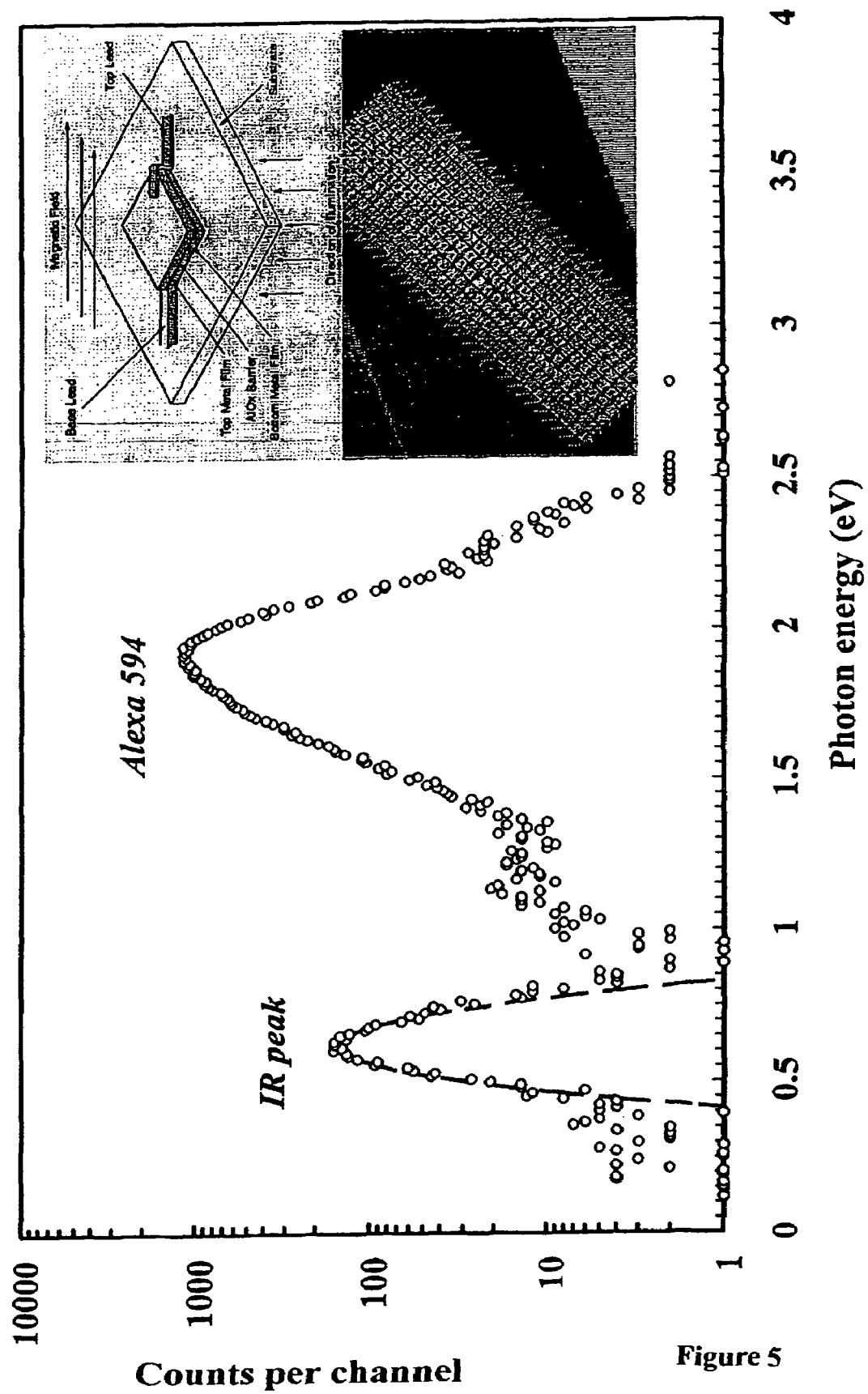

FIG. 5 shows the STJ pulse height spectrum (logarithmic scale) of Alexa 594. Leica I3 filter set. Broken curve—gaussian fit to IR peak. Top Inset—schematic of STJ operation. Lower Inset—Nomaski microscope image of 10×32 pixel STJ array.

Figure 6:
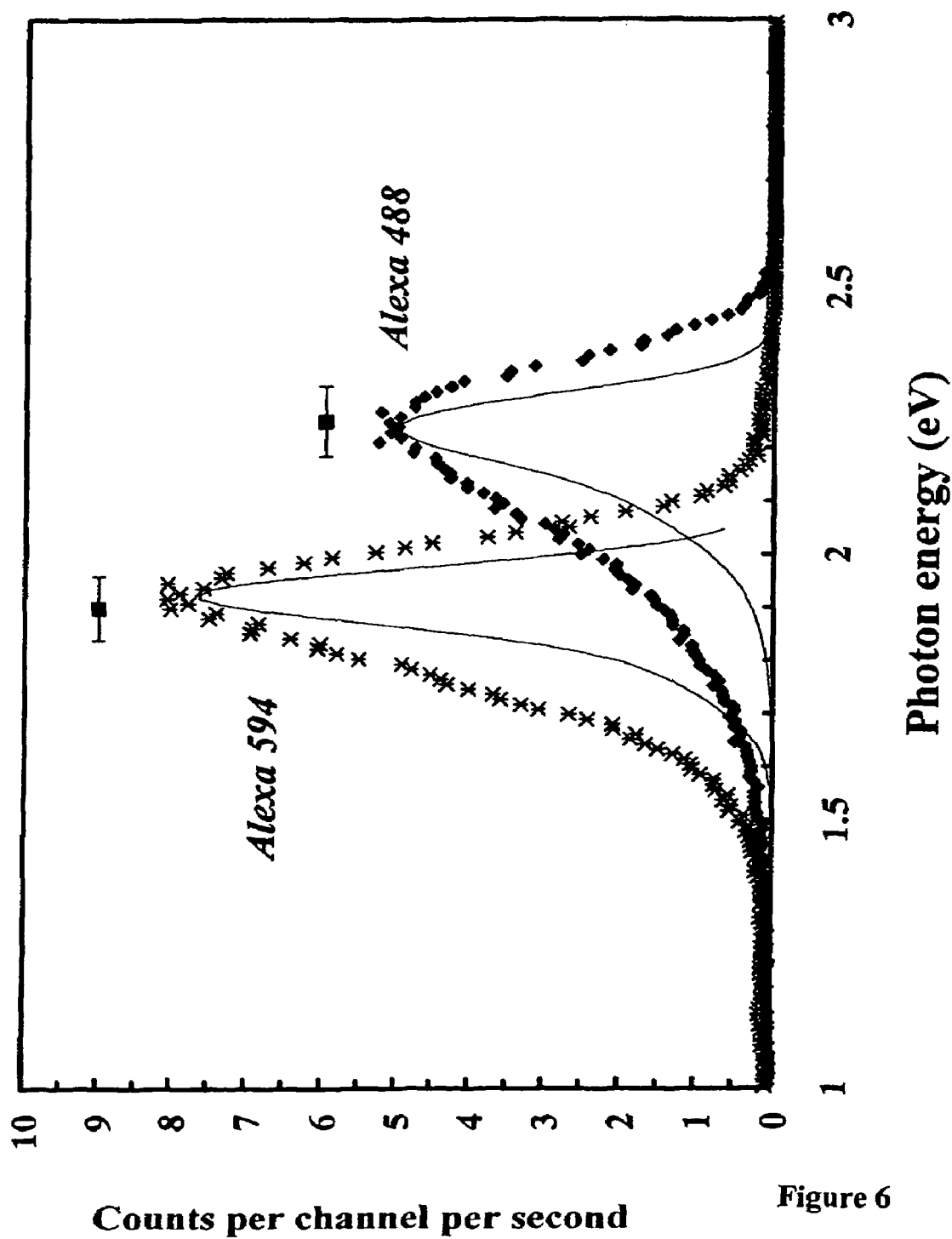

FIG. 6 provides overlaid Alexa 594 and 488 spectra (individual symbols). Leica I3 filter set. Full curves—manufacturer's emission spectra, corrected for optical fibre transmission and STJ quantum efficiency. Finite resolving power of the detector indicated by FWHM energy resolution "error bars".

Figure 7:
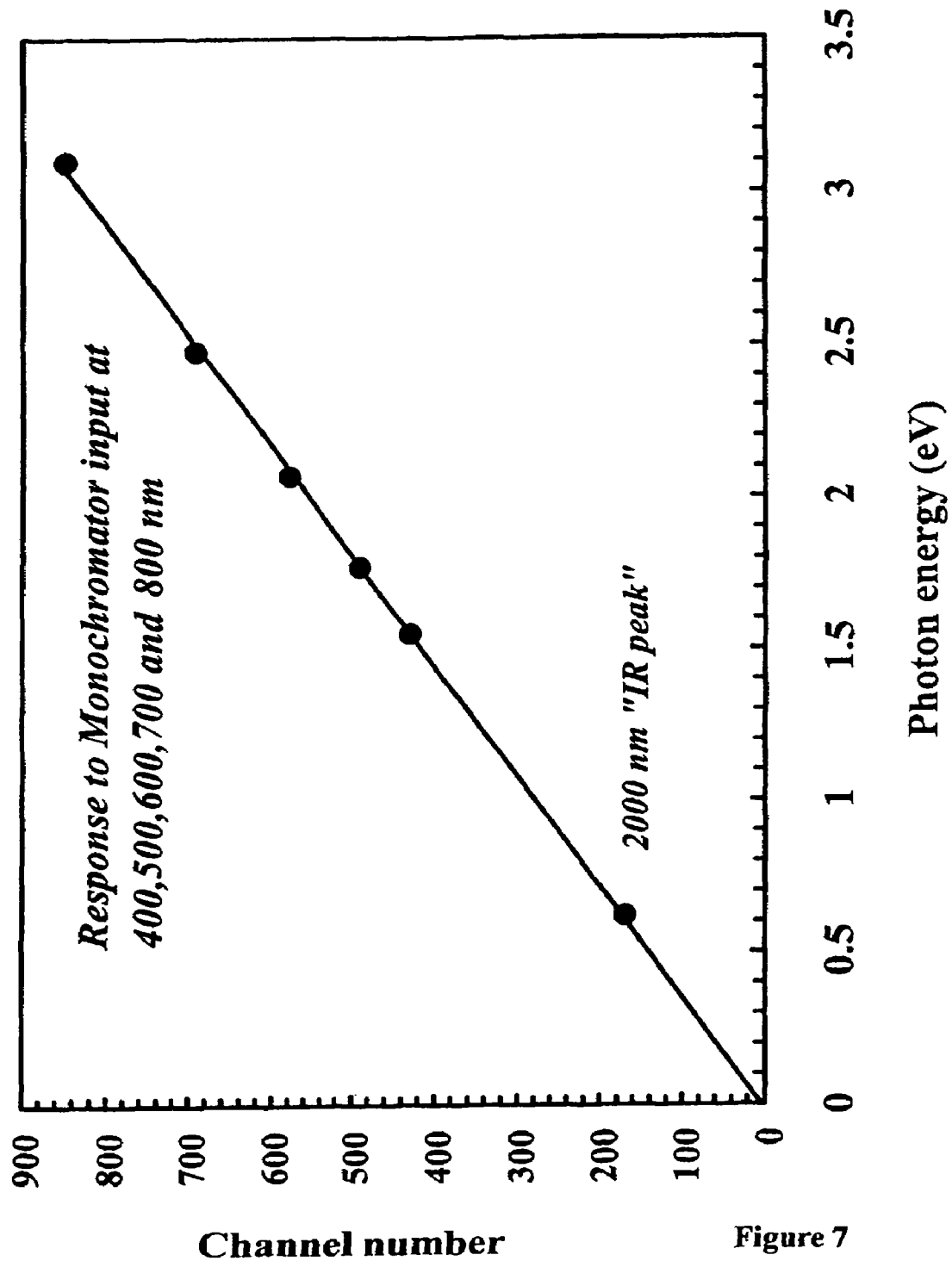

FIG. 7 gives the STJ pulse height calibration, indicating excellent detector linearity.

Figure 8:
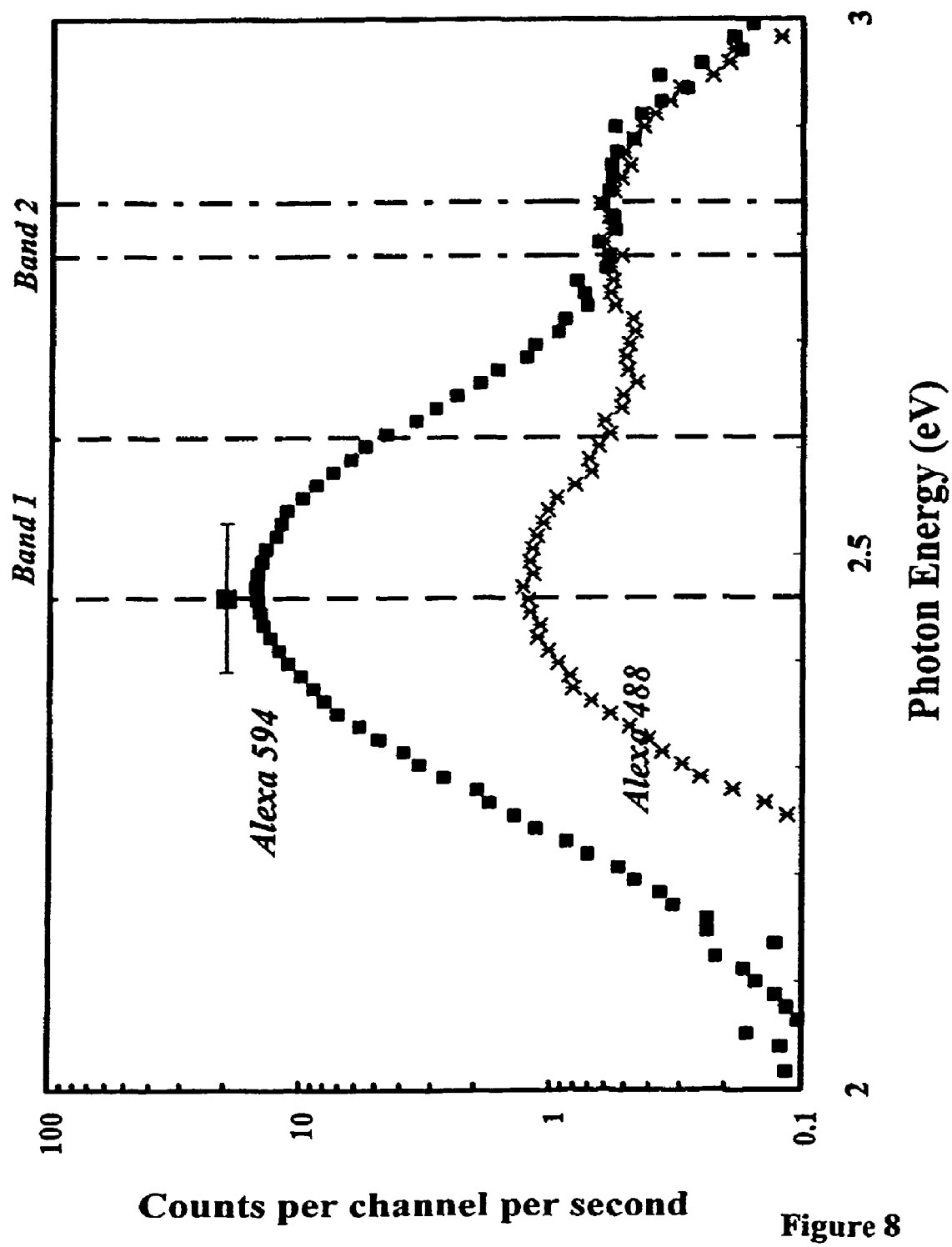

FIG. 8 provides overlaid Alexa 594 and 488 spectra. Adapted Omega filter set.

Figure 9:
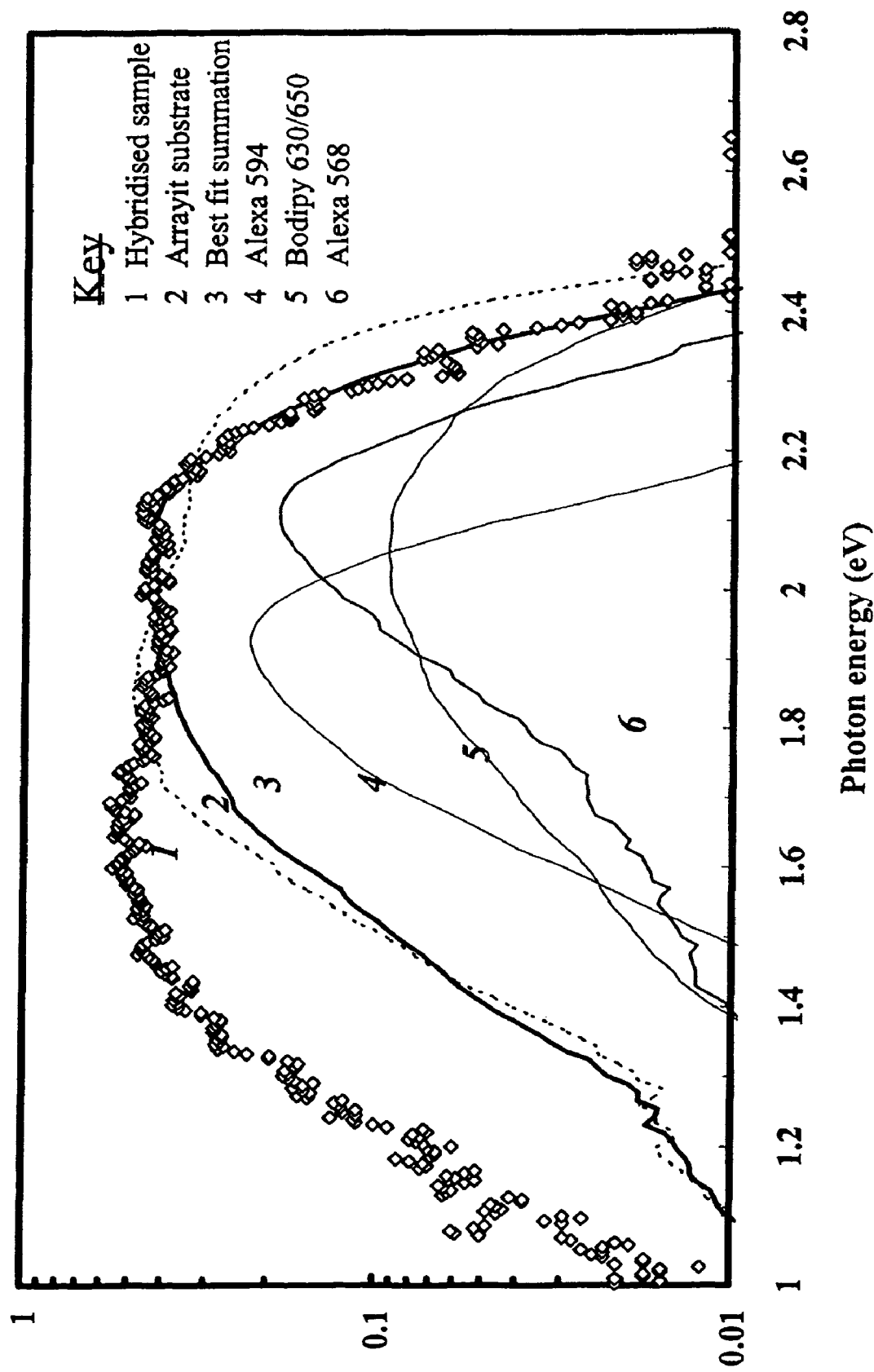

FIG. 9 is an analysis of composite fluorescence spectrum from genetic material hybridised to three probes.

Figure 1:
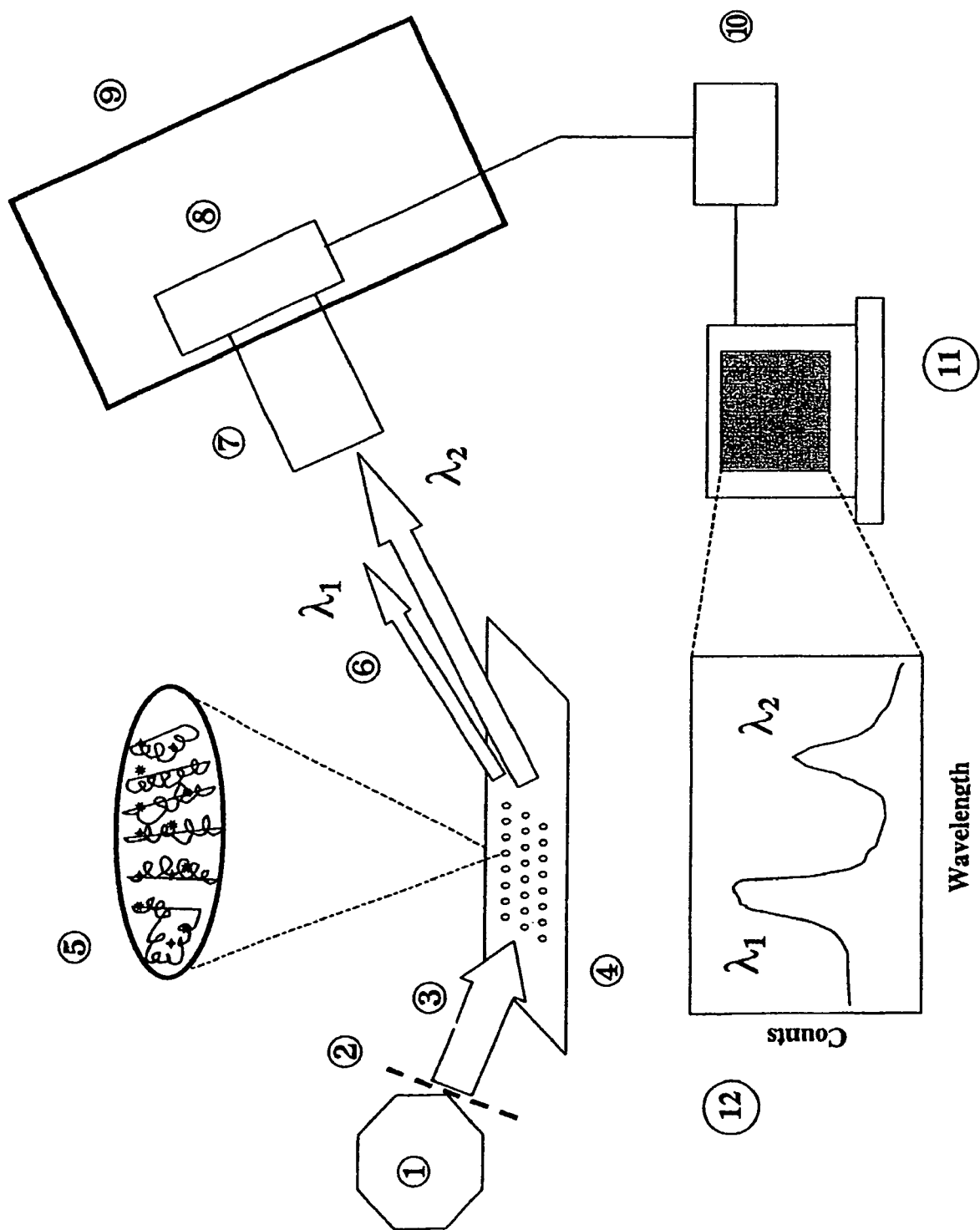
FIG. 1 illustrates a detection system in accordance with the present invention.

The following key applies to FIG. 1:

1 Excitation light source
2 Input filter (if required)
3 Incident light beam
4 Microarray on standard format substrate
5 (Inset) hybridised DNA in one microarray cell, probe strands bearing (as illustration) two fluorochromes
6 Fluorescent emission from fluorochromes, peak emission wavelengths $\lambda_1$ and $\lambda_2$
7 Output optics
8 Wavelength resolving, photon counting detector array
9 Cryostat
10 Amplification and signal processing
11 Spectral processing, fitting and display
12 (Inset) Intensity versus wavelength spectrum, showing resolution fluorochrome emissions.

EXAMPLES OF THE INVENTION

We adopt the following terminology:
Support: that to which the target is bound.
Target: unlabelled molecules that are bound to the support.
Probe: labelled molecules in the solution that will hybridise or bind to the target.

Some researchers reverse the definitions of probe and target.

The target can be any biological molecule, DNA, RNA, synthetic oligonucleotide, peptide or protein. DNA can be cDNA (that is, genes as RNA copied enzymatically to the DNA form), genomic DNA or RNA, clones in any vector such as plasmids, lambda, BACs, YACs), subsets of total genomic DNA coming from one or several chromosomes. RNA and DNA can come from any organism (plants, animals, viruses, bacteria, fungi or any of their subsets) and any tissue. Synthetic oligonucleotides should be at least 15 bp long and can be up to 100 bp, based on a known DNA or RNA sequence, random or with modified nucleotides at any position.

The probe can be any RNA or DNA or antibody, and is specifically labelled for recognition. In any given experiment preferably 3-10 or more different probes are used and need to be labelled differentially. In most cases the probe will be the total amount, or suitable subset of RNA or DNA from two or more different species, varieties or populations, or individuals at different environmental conditions, developmental stages etc.

The support may be of any material to which the target will bind. The support may conveniently be a standard microscope slide, typically having dimensions of 76×26 mm. However, the support may also be a chip of any appropriate size. Suitable materials for the slide or chip are glass or metal. The support will usually be coated or charged in order to facilitate the binding of the target. Examples of suitable coatings are poly-L-lysine, amino-silanes, cellulose, and other biological molecules.

Example 1

In many cancer biopsies, it is necessary to take multiple biopsies of a tissue to find the cancerous cells. Currently, a microscope slide preparation is made from each biopsy, and examined by skilled observers to find the status of each. With the array and detector technology of the present invention, DNA genetic material or RNA expressed genes from each of say five biopsies along with five control samples— from known cancers of different stages or types, and normal samples from unaffected controls and the patient—would be isolated (automated), labelled with different fluorochromes and hybridised to the array. If any samples show abnormalities, this will be immediately detectable by the different ratio of hybridisation of the probes to the different target on the slides. Current technologies have poor quantification, and are unable to distinguish the number of probes required for careful control and different types of cancer.

Example 2

Abnormal expression of five to ten genes is frequent in many disease syndromes. DNA or RNA from individual samples is placed onto the support surface as target and then hybridised with five gene sequences labelled in different colours. The hybridisation of each spot on the array is then examined and differences from the control indicate that a sample is abnormal.

Example 3

Some (but not all) wild species related to crop plants, e.g. bananas, are resistant to diseases such as fungal diseases, but these are very different from each other and susceptible commercial crop varieties. We will place many thousands of plant genes or other DNA sequences onto the array, and hybridise with DNA or RNA from resistance and susceptible plants, using 10 at a time each labelled with a different fluorochrome. Where a target hybridises with only probes from all resistant accessions, it is a candidate resistance gene. Those hybridising to probes from only a few resistant accessions are probably genes showing inter-accession variability, so the use of multiple probes is essential to remove such false results.

Example 4

Many disease syndromes arise from the inability of the body to make a particular chemical, but the lack of the chemical may arise from failure of any step in a multi-step process of biosynthesis. Although the disease symptoms are the same, a different pharmaceutical treatment might be used depending on the step that fails. DNA (or RNA/cDNA) from patients suffering from the syndrome might be extracted and placed as a target, which is then hybridised with probes for each of the genes involved in the biosynthesis (and control genes). The probe not found to hybridise represents the gene that is deficient in the patient.

Example 5

Current technologies require high purity of the DNA/RNA sample for hybridisation analyses. Because of the high sensitivity and high background discrimination of the proposed system, the number of controls of hybridisation that can be included, and the possibility of using additional detection channels to quantify amounts of target present, crude or minimally prepared (e.g. squashing the tissue onto the substrate, with or without further solution treatments) cell preparations may be used to obtain high-quality data. Thus whole cells could be squashed on the support, and probed with multiple DNA probes, and stains to measure amount of cellular material bound, to diagnose expression of a gene related to a disease.

Example 6

Proteins can be placed on the array, and hybridised against labelled antibodies. It might also be that unlabelled proteins have a characteristic enough fluorescence, or even transmission/reflectance/autofluorescence/absorbance spectrum ('colour') that they can be identified in proteinaceous samples.

Example 7

The system can be used to test the distribution of specific repetitive DNA among a group of plant species for their diversity and distribution: e.g. retroelement clones isolated from a range of related or unrelated species as targets; total genomic DNA from various related or unrelated plant species, e.g. conifer or Brassica species, as probes. This shows the evolutionary distance between species and the potential of using them in breeding programmes.

Example 8

The system can be used to test the allelic variability of DNA sequences or genes: e.g. synthetic oligonucleotides representing all possible nucleotide changes in defined region of a repetitive or low copy DNA sequence of a e.g. repetitive DNA family, centromeric DNA, a multigene family, rDNA, disease-associated or resistance proteins, storage proteins, as targets. Total genomic DNA from species, varieties, populations or individuals from related or unrelated individuals or species as probes.

Example 9

The system can be used to test the existence, variability and expression of disease generating organisms in a range of host species; e.g. virus DNA (clones or oligonucleotides) as targets, total genomic DNA of different individuals as probes.

Example 10

A survey wishes to find the frequency of different forms of a particular gene (alleles) occurs in a population. DNA from thousands of individuals is extracted and put onto an array.

Example 11

A cell contains a particular enzyme which is characteristic of its state following particular treatment. A substrate is applied to the cell which has the property of chemiluminescence. This light emission is detected with the cryogenic detector.

Examples 12 to 14

Examples 12 to 14 are model experiments that show the utility of the present invention on model systems comprising fluorochromes (probes) bound to biological molecules (targets). In each of these three Examples, the cryogenic detector used was that at the Research and Technology Centre for the European Space Agency, ESTEC, Noordwijk, Holland, which is a cryogenic superconducting tunnel junction (STJ) detector running at approximately 300 mK (milliKelvin) temperature, using a 30 μm×30 μm detector.

Example 12

The cryogenic detector was used to collect fluorescence emission spectra from a number of different, commercially available, labelled nucleotides and fluorochromes conjugated to other moieties, namely:

LR_C: Fluorored (rhodamine-4-dUTP, RPN2122), Amersham Pharmacia Biotech, Little Chalfont, Buckinghamshire, UK FG_C: Fluorogreen (fluorescein-11-dUTP, RPN2121), Amersham Pharmacia Biotech, Little Chalfont, Buclinghamshire, UK A48_C: Chromatide Alexa Fluor (488-5-dUTP), Molecular Probes, Eugene, Org. USA A59_C: Chromatide Alexa Fluor (594-5-dUTP), Molecular Probes, Eugene, Org., USA Fluorochrome Conjugated Moieties
TR_C: Texas Red avidin D (A-2006), Vector Laboratories, Burlingame, Calif., USA FI—C: Fluorescein streptavidin (FITC; SA-5001), Vector Laboratories, Burlingame, Calif., USA The above samples were spotted by hand onto a standard glass microscope slide.

The fluoresence emission spectrum was also collected from a sample of Whatman filter paper No. 1 (FIL-C), which contains fluorescent brightening agents.

Figure 2:
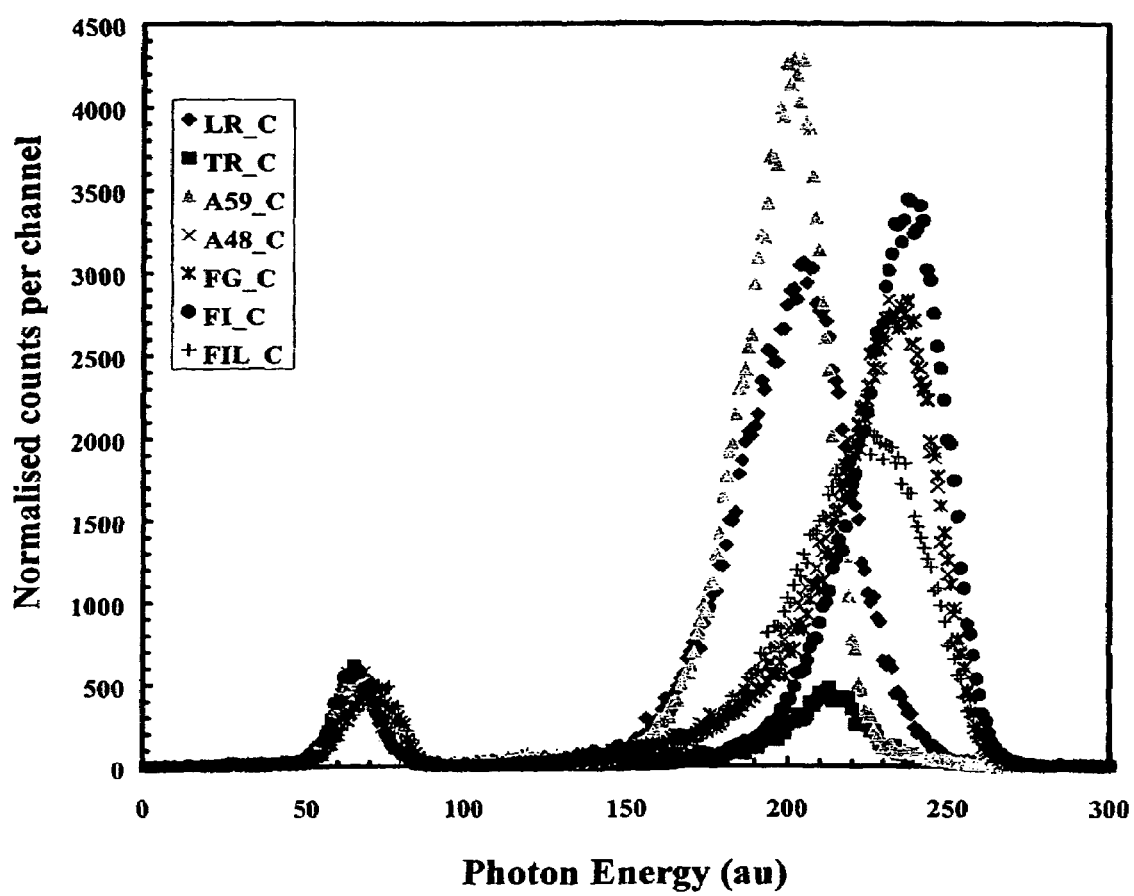
FIG. 2 shows fluorescence emission spectra collected by cryogenic detector from a number of labelled nucleotides and fluorochromes conjugated to other moieties.

A Leica fluorescent microscope and Mercury Lamp (W100) as fluorescent light sources and a filter set with 340-380 nm (near-UV) excitation and long-pass 425 nm emission filter (Leica set A) were used for excitation of the fluorochromes. The spectra obtained are shown in FIG. 2. Even though excited far from the maximum, good spectra were obtained from fluorochromes emitting in the red area (Alexa 594, Fluorored, and Texas red), while strong spectra in the green region were obtained from those fluorochromes with more suitable characteristics (Fluorogreen, FITC and Alexa 488). All spectra had characteristic shapes, maxima and areas. Photon levels counted not originating from the fluorochromes and below 1 micrometer wavelength were not detectable, and collection of spectra without the fluorescent light source on were approximately four photons per minute (including electronic noise which has different pulse characteristics and hence can be filtered out) compared to rates of 5000 to 50000 per minute typically obtained from the fluorochromes.

The experiment shows 1) the cryogenic detector can detect characteristic fluorescent emission spectra from commonly used fluorochromes in biology. 2) the detector has minimal levels of background (typically 0.01%) giving extremely clean spectra. 3) emission spectral shape, even with single excitation wavelength bands, allows separation of individual fluorochromes. 4) brightness can be exactly quantified by photon counts. 5) extremely low levels of fluorochromes can be measured.

Example 13

Figure 3:
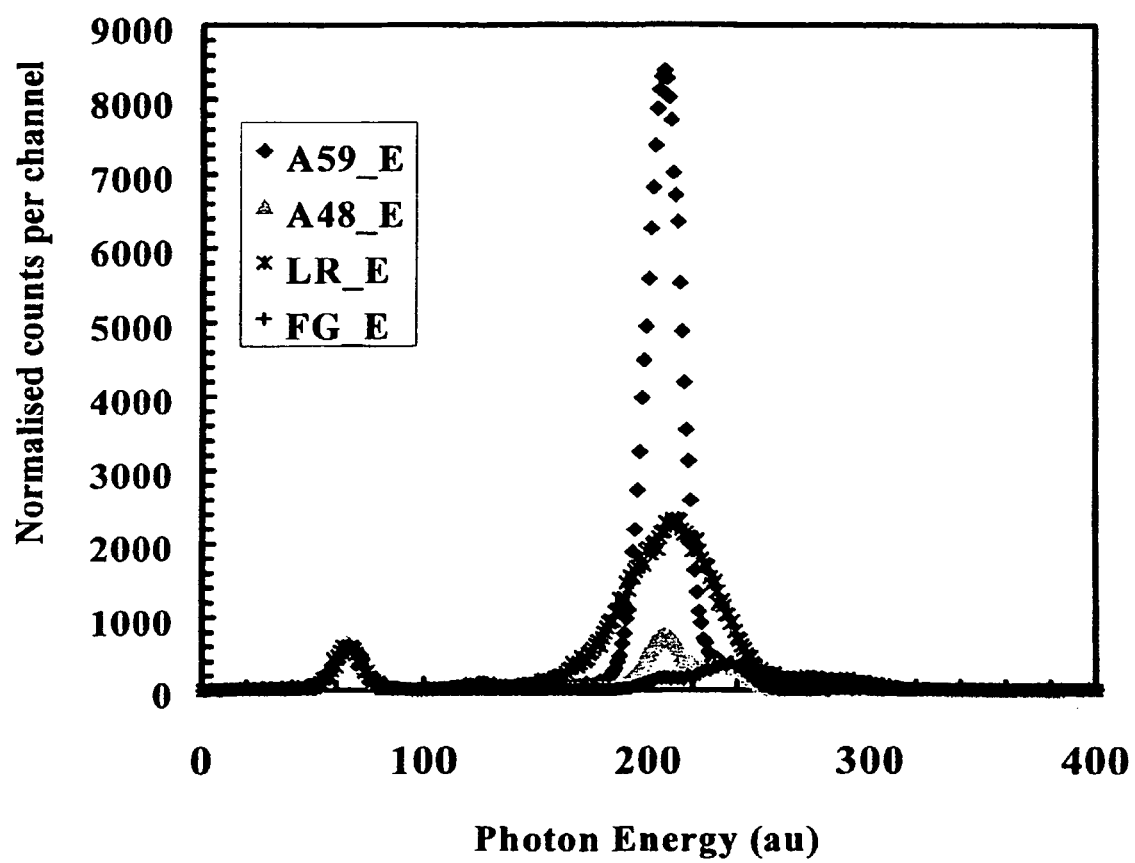
FIG. 3 shows further such fluorescence emission spectra.

Spectra were obtained for four of the fluorochromes used in Example 11, using the same conditions, except that the filter Leica 13 was used. The spectra are shown in FIG. 3.

Example 14

The cryogenic detector was used to collect fluorescence emission spectra from a sample of paper containing fluorescent brightening agents, namely the white area of a self-adhesive address label printed by Abel-Label, Northampton, UK.

Figure 4:
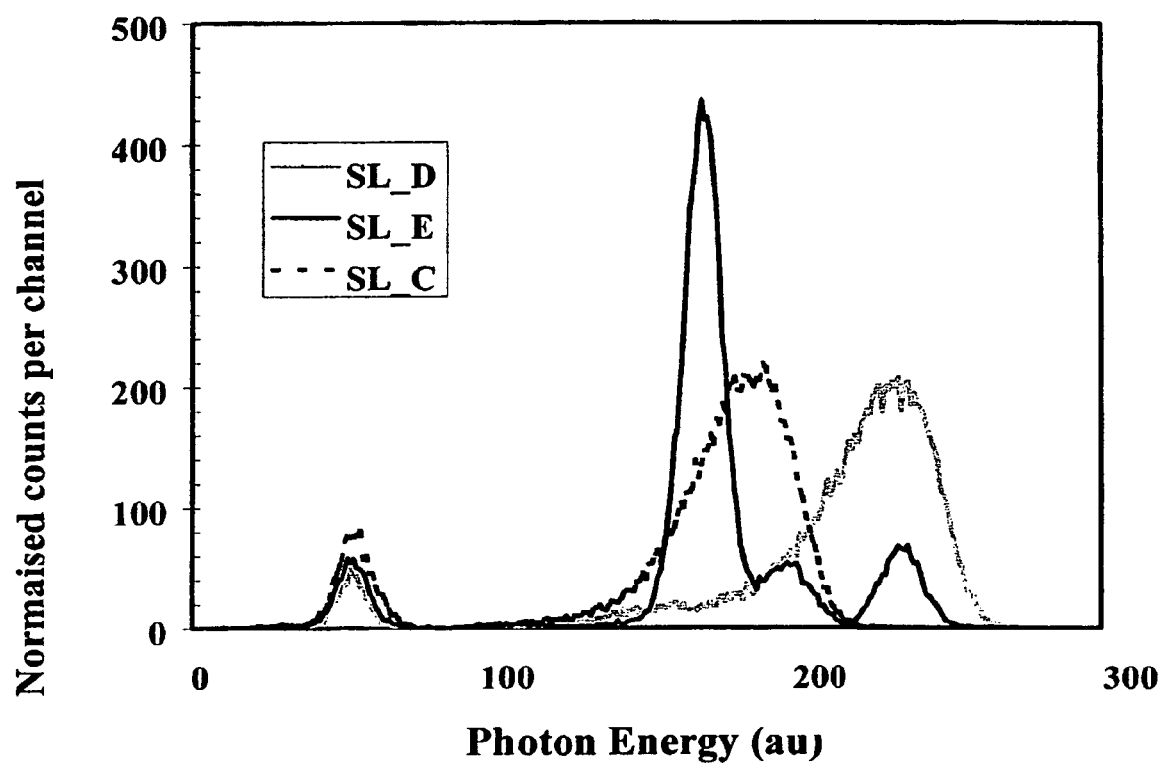
FIG. 4 shows fluorescence emission spectra collected from a sample of paper.

This demonstrates the characterisation of the staining of cellulose and other cellular components by stains of the fluorescent brightener class. The spectra were obtained with UV excitation and long-pass blue emission (line SL_D, Leica filter set A), blue excitation, long-pass green emission (SL_C, Leica filter set I3) and with triple bandpass filter (SL_T, Omega Optical XF56 filter set). The spectra are shown in FIG. 4. This experiment demonstrates the utility of the method for 1) characterising the nature of unknown fluorochromes used as stains; 2) detecting the nature or composition of stained objects of biological or other origin using stains of known specificity; 3) detecting the quantity of stained objects of biological or other origin.

Example 15

A more detailed experimental investigation was carried out, as reported follows:

The Detection of Multiple Fluorescent Labels Using Superconducting Tunnel Junction Detectors The simultaneous measurement of the optical emission from collocated fluorochromes is a common problem in biology. Imaging cell components demands the temporal registration of multiple fluorescent markers such as variants of Green Fluorescent Protein (GFP). In Fluorescent Resonant Energy Transfer (FRET), changes in emission spectra indicate the physical separation between donor and acceptor dye molecules. Quantifying the hybridisation of labelled nucleic acids (probes) to immobilised target molecules in microarray format or in cells in situ ideally requires the efficient, artefact-free measurement of several fluorescent spectra simultaneously, see reference 1.

Cryogenically-cooled Superconducting Tunnel Junction (STJ) detectors, see references 2-6, developed for astronomy measure the energies of individual optical photons with very low levels of internal background. Here, we show that STJs can be used for the sensitive registration of multiple biological fluorochromes. Using a single near-UV excitation filter, and standard dichroic and long-pass filters, the emission spectra of common fluorochromes could be easily distinguished—from each other and from broadband substrate fluorescence.

Cryogenic detectors have the potential to revolutionise quantitative multifluorochrome imaging in biology.

Photomultiplier tubes (PMTS) and image intensifiers are the photon-counting detectors most commonly used to image weakly fluorescent biological specimens. These detectors provide information on photon colour (energy or wavelength) only when used with narrow band output filters or dispersive gratings. Their efficiency is limited by the quantum yield Q electrons/photon of the PMT photocathode. For a photocathode such as S20 (CsKNaSb), see reference 7, Q<20% in the optical band. Grating-based systems do now offer up to 32 parallel energy channels, see reference 8, each read out by an independent PMT, but the instrument sensitivity remains limited by the photocathode's thermionic dark noise count rate $-B \geq 10$ counts.cm-2.s-1 at room temperature, see reference 9. More commonly, the fluorochromes are addressed sequentially, repeatedly scanning the sample and registering the fluorescence through a series of narrow band output filters. Multiple scanning increases the possibility of photobleaching.

The low throughput of dispersive spectrometers was one of the motivations for the development in astronomy in the nineteen-nineties of cryogenic, energy-resolving detectors such as the STJ and the Transition Edge Sensor (TES), see reference 10. An STJ consists of two superconducting layers held at a temperature T well below their superconducting-to-normal transition temperature Tc, and separated by an insulating oxide layer (see upper inset to FIG. 5). For T~Tc/10, the thermally induced tunnel current is negligible and the absorption of a photon of wavelength λ (nm) gives rise to a number $N_o \sim 7 \times 10^5 / \lambda \Delta(T)$ of excess free charges (quasiparticles) where Δ (meV) is the superconducting energy gap, see reference 4. The intrinsic (or "tunnel limited") resolving power R=λ/Δλ of a symmetrical STJ is then:

$$R = 357[\lambda\Delta]^{-1/2}[1+F+1/\langle n \rangle]^{-1/2} \quad \text{Equation-(1)}$$

where: F is the Fano factor (~0.22 for transition metal superconductors, see reference 6) and <n> is the average number of times that each quasiparticle tunnels across the barrier.

The detector used in our initial study of biological fluorescence was a single 30×30 μm2 STJ with 100 nm thick Ta layers and 30 nm thick Al layers on either side of the tunnel barrier. The transition temperature for bulk tantalum is 4.5 K and the energy gap Δ(0) is 0.69 meV. The detector was made using photo-lithographic techniques from an Ta/Al multi-layer deposited on a polished sapphire substrate. The low leakage current (<0.1 pA/μm2) gave a negligible contribution to the baseline noise floor, while the high transparency of the barrier resulted in high signal amplitudes.

The detector had a responsivity $\langle n \rangle N_o \sim 40000$ tunneled electrons per eV of photon energy, and a pulse decay time of ~20 μs. Eq. (1) then indicates resolving powers of 16.0 and 8.8 at wavelengths of 600 nm and 2000 nm. Calibration using monochromatic radiation indicated R (600 nm)~13.3. Cooling to 300 mK in a 3He cryostat (i.e. T~Tc/15) kept the thermally-excited quasiparticle current well below the leakage current level. We would then expect the dominant background source in the STJ to be cosmic ray muons interacting with the sapphire substrate, in a complex manner, to create pair-breaking phonons at an upper limit rate B~0.01 cm-2 s-1.

Given a peak STJ quantum efficiency Q (600 nm) of 75%, see reference 4, we then arrive at the sensitivity advantage of the cryogenic detector over a PMT-based system:

$$\frac{\{Q_{STJ}/\sqrt{B}_{STJ}\}}{\{Q_{PMT}/\sqrt{B}_{PMT}\}} = 120 \text{ times} \quad \text{Equation (2)}$$

Light from a Leica Aristoplan epifluorescence microscope with a 100 W Osram HBO mercury excitation source was coupled into the back-illuminated STJ via a 6 meter Oriel 77530 UV-grade fused silica fibre, bandpass λ~200-2000 nm. The STJ quantum efficiency exceeds 50% for λ values between 150 and 700 nm. No efforts were made to focus the light from the specimen onto the fibre or from the end of the fibre onto the detector. The coupling efficiency was therefore extremely low (<0.01%). The detector was held within a light tight shield at the base system temperature of 300 mK. The warm end of the optical fibre, however, constitutes a 300K black body source which, when convolved with the fibre transmission, provides an effective reference signal in all STJ spectra at a wavelength of 2 microns (see FIGS. 5, 7).

The warm readout electronics consisted of a charge sensitive preamplifier situated ~1 m from the detector, a shaping amplifier (10 μs shaping time) and an Analogue to Digital (AD) converter whose output was optically coupled to a PC, on which the pulse amplitude and decay time was recorded for each detected photon. A pulse risetime window was applied to select valid events.

Fluorescence spectra were measured from eleven different, commercially available, labelled uridine nucleotides. Six different substrates were also examined. Four excitation filters were used: the spectra presented here were obtained with the following two filter sets: Leica filter set I3; 450-490 nm excitation, 510 nm dichroic cutoff and 515 nm long-pass filter.

(iii) Omega Optics Inc. 11XF56 triple excitation filter, with transmission bands centred on 457, 528 and 633 nm, its associated dichroic mirror and an Omega 580 long-pass emission filter. The transmissions of the actual filters used were confirmed post facto using a spectrophotometer.

Even though excited far from maximum absorbance, spectra were obtained from fluorochromes emitting in the red (Alexa 594, Fluorored and Texas Red) and green (Fluorogreen, Avidin FITC and Alexa 488). We illustrate the potential of the STJ for fluorescent imaging with particular reference to the dyes Alexa 488 and Alexa 594 12. FIG. 5 shows the pulse height spectrum of the latter fluorochrome with the Leica I3 filter set. The spectrum is cut off at 2.4 eV (515 nm) by the long-pass filter. Even with the fluorochrome excited at only ~3% of maximum absorbance, the signal-to-background (peak channel count divided by average channel count at energies just above the IR peak) is at least 275:1. Fitting a normal distribution (the broken curve) to the IR peak indicates R (2000 nm)=4.0.

Injecting a known charge to the warm STJ preamplifier from an electronic pulser produced a peak width of 0.084 eV FWHM. The quadrature sum of tunnel limit and electronic noise contributions then implies a 2 micron resolving power R=5.7, slightly better than observed.

For each fluorochrome, the microscope focus was adjusted to produce an output count rate of 800 Hz—the maximum rate before pulse pile-up compromised the spectral resolution. The "dark" count rate obtained by closing the microscope shutter between bulb and filter was $0.09^{s-1}$. Because individual spectra were not obtained at constant intensity, overlaying two STJ spectra does not necessarily represent the degree of spectral separation for the corresponding mixture of fluorochromes. Nevertheless, FIG. 6 indicates that, while the degree of spectral overlap is significant, it is straightforward to deconvolve the relative intensity contributions of mixed Alexa 488 and 594 probes. We note that the peak emission energies and spectral widths for both probes differ significantly from the templates published by the manufacturer, see reference 12. Since the STJ calibration rules out any "zero shift" in the detector response (see FIG. 7), we conclude that these measurements constitute evidence for the influence of local environment on fluorochrome emission. Here, the dyes dried out from solution spotted onto glass cleaned with chromic acid.

FIG. 8 shows the Alexa 594 and 488 spectra obtained with the Omega triple filter set; the "top hat" transmission bands of the output filter are indicated by the broken vertical lines. This figure shows that the spectroscopic capability of the STJ may be combined with appropriate selections of input and output filters to give highly preferential registration of one fluorochrome.

FIG. 9 illustrates the application of the STJ to the study of genetic material hybridised, on an Arrayit™ substrate, see reference 13, with multiple probes (Alexa 568, Alexa 594 and Bodipy 630/650— all produced by Molecular Probes Inc., see reference 12). Data set 1 represents the measured sample spectrum, while curves 2,4,5,6 are the component spectra measured for the three fluorochromes separately and for the substrate. Curve 3 indicates that a linear sum of the component intensities with weights:

Alexa 568: Bodipy: Substrate: Alexa 594=10:10:4:3 provides an excellent fit to the data in the 1.9-2.4 eV (515-652 nm) band.

We cannot attribute the excess intensity at lower energies to the presence in the sample of unhybridised DNA, since the intrinsic fluorescence of DNA is well known to peak in the UV. An alternative explanation is excimer (excited dimer) emission arising as a result of the high concentrations of the fluorochrome probes in the sample.

In summary, we have shown that a cryogenic detector can detect, quantitatively and at very high signal-to-noise compared to conventional system, characteristic fluorescent emission spectra from fluorochromes commonly used in biology. Even with single excitation wavelength bands, registration of the complete spectrum allows separation of multiple fluorochromes. Remarkably, we found that non-focussed, low levels of peripheral sample illumination with Philips TLD 36 W/83 fluorescent tubes (i.e. normal laboratory lighting) were able to excite count rates in excess of 1000 Hz.

The present Ta technology (R~10–20) is compatible with at least four simultaneous labels with a single excitation filter; the potential of Hf ($\Delta(0)$=0.02 meV; R~80) and Mo ($\Delta(0)$= 0.14 meV; R~40) for better resolution (at lower operating temperatures) is well documented, see reference 4. In the context of microarray readout, any increase in the number of labels that can be measured without interference is important because either increased numbers of internal controls can be included, or more samples can be tested simultaneously. The modest count rate limitation of a single STJ pixel can be overcome by using parallel arrays; 6×6 element Ta STJ matrices have been fabricated and the development of 10×32 Mo arrays studied by the ESTEC group (see lower inset to FIG. 5). These developments and the production of closed cycle cooling systems for the T<100 mK regime will have an important bearing on the ultimate utility of optical STJs in the life sciences.

DOCUMENTS

1. T. Schwarzacher and J. S. Heslop-Harrison, "Practical in situ hybridisation", Bios, Oxford (2000) pp 213.
2. M. A. C. Perryman, C. L. Foden & A. Peacock, "Optical photon counting using superconducting tunnel junctions", Nucl. Instrum. Meth. A325, 319-325 (1993).
3. A. Peacock, P. Verhoeve, N. Rando, A. van Dordrecht, B. G. Taylor, C. Erd, M. A. C. Perryman, R. Venn, J. Howlett, D. J. Goldie, J. Lumley & M. Wallis, "Single optical photon detection with a superconducting tunnel junction", Nature 381, 135-137 (1996).
4. P. Verhoeve, N. Rando, A. Peacock, A. van Dordrecht, A. Poelaert & D. Goldie, "Superconducting tunnel junctions as photon counting detectors in the infrared to the ultraviolet", IEEE Trans. Appl. Supercon., 7, 3359-3362 (1997).

N. Rando, J. Verveer, S. Andersson, P. Verhoeve, A. Peacock, A.

Reynolds, M. A. Perryman & F. Favata, "S-Cam: a spectrophotometer for optical astronomy: performance and latest results", Rev. Sci. Instr. 71, 4582-4591 (2000).

N. Rando, A. Peacock, A. van Dordrecht, C. L. Foden, R. Engelhardt, B. G. Taylor, P. Gare, J. Lumley & C. Pereira, Nucl. Instr. Meth. A 313, 173-183 (1992).
7. A. H. Sommer, "Photoemissive materials", Wiley (New York), (1968).
8. META detector for the Carl Zeiss LSM 510 confocal microscope. Carl Zeiss, Welwyn Garden City, Herts, UK.
9. I. G. Butler et al., "Performance of a large area MCP photon counting intensifier". Proc. SPIE 2278, 126-30 (1994).
10. R. W. Romani, A. J. Miller, B. Cabrera, S. W. Nam and J. M. Martinis, "Phase resolved Crab studies with a cryogenic TES spectrophotometer", Ap. J, in press (2002).
11. Omega Optics Inc, 210 Main Street, Brattleboro, Vt. 05301, USA.
12. N. Panchuk-Voloshina et al., "Alexa dyes, a series of new fluorescent dyes that yield exceptionally bright, photostable conjugates", J. Histochemistry & Cytochemistry 47 (1999) 1179-88.
13. TeleChem International Inc., 524 E. Weddell Drive, Suite No. 3, Sunnyvale, Calif. 94089, USA.

All publications, patents, and patent documents, cited in this application, are incorporated by reference herein, as though individually incorporated by reference. In the case of any inconsistencies, the present disclosure, including any definitions therein will prevail. The invention has been described with reference to various specific and preferred embodiments and techniques. However, it should be understood that many variations and modifications may be made while remaining within the spirit and scope of the invention.

What is claimed is:

1. A method of detecting photons in a biological assay comprising
   (a) generating photons from a fluorochrome present in said biological assay;
   (b) transmitting said photons to a cryogenic detector using an optical fibre, said cryogenic detector comprising said optical fibre and a photon capture element operating close to or below a temperature at which said photon capture element exhibits superconducting properties; and
   (c) detecting said photons with said cryogenic detector.

2. The method of claim 1, wherein the fluorochrome emits a fluorescence and said photons are from the fluorescence.

3. The method of claim 1, wherein the detector detects stimulated emission of said photons generated from said fluorochrome.

4. The method of claim 1, wherein said fluorochrome is a label.

5. The method of claim 2, wherein the photons are detected across a fluorescence emission spectrum.

6. The method of claim 2, wherein the fluorescence is detected in a range of wavelengths covering ultraviolet light to infra-red light.

7. The method of claim 1, wherein the fluorochrome is conjugated to a nuclrotide which is incorporated into a DNA probe and the biological assay further comprises an immobilized nucleic acid.

8. The method of claim 7, wherein the immobilized nucleic acid hybridizes with the DNA probe.

9. The method of claim 1, wherein the detector has a single detector element.

10. The method of claim 1, wherein the detector has two or more detector elements.

11. The method of claim 1, wherein the biological assay further comprises two or more different fluorochromes and the detector detects fluorescences emitted by said fluorochromes.

12. The method of claim 11 wherein said different fluorochromes are distinguished from each other by their different time gaps between excitation and emission.

13. A method of forming a bioimage comprising:
   (a) genetrateing photons from a fluorochrome present in a biological assay;
   (b) transmitting said photons to a cryogenic detector using an optical fibre, said cryogenic detector comprising said optical fibre and a photon capture element operating close to or below a temperature at which said photon capture element exhibits superconducting properties; and
   (c) detecting said photons with the cryogenic detector, generating photon data, and form a bioimage.

14. The method of claim 13, wherein said photon data is evaluated.

15. A method of forming quantitative fluorochrome bioimage comprising:
   (a) generating photons from a fluorochrome present in a biological assay;
   (b) transmitting said photons to a cryogenic detector using an optical fibre, said cryogenic detector comprising said optical fibre and a photon capture element operating close to or below a temperature at which said photon capture element exhibits superconducting properties;
   (c) detecting said photons with the cryogenic detector; and
   (d) generating photon data and forming a fluorochrome bioimage which is quantitated.

16. The method of claim 15, wherein the detector generates fluorescent data which is acquired and evaluated based on said photon data.

* * * * *

UNITED STATES PATENT AND TRADEMARK OFFICE
CERTIFICATE OF CORRECTION

PATENT NO. : 7,585,624 B2
APPLICATION NO. : 10/794397
DATED : September 8, 2009
INVENTOR(S) : Fraser et al.

It is certified that error appears in the above-identified patent and that said Letters Patent is hereby corrected as shown below:

In column 15, line 28, in Claim 7, delete "nuclrotide" and insert -- nucleotide --, therefor.

In column 16, line 9, in Claim 13, delete "generateing" and insert -- generating --, therefor.

Signed and Sealed this

Twenty-second Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,585,624 B2  Page 1 of 1
APPLICATION NO. : 10/794397
DATED : September 8, 2009
INVENTOR(S) : Fraser et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 789 days.

Signed and Sealed this

Fourteenth Day of September, 2010

David J. Kappos
*Director of the United States Patent and Trademark Office*